United States Patent
Hollander et al.

[11] Patent Number: 5,921,434
[45] Date of Patent: Jul. 13, 1999

[54] DISPOSABLE GLOVE DISPENSER

[76] Inventors: Kenneth A. Hollander, 719 Los Pueblos Dr., Camarillo, Calif. 93012; David Bitran, 17506 Burma St., Encino, Calif. 91316

[21] Appl. No.: 09/048,386

[22] Filed: Mar. 26, 1998

[51] Int. Cl.⁶ .................................................. B65H 1/00
[52] U.S. Cl. .............................................. 221/34; 221/63
[58] Field of Search .................. 221/33, 34, 63; 206/278; 211/51, 53

[56] References Cited

U.S. PATENT DOCUMENTS

| | | | |
|---|---|---|---|
| 375,010 | 10/1887 | Karnes | D6/515 |
| 3,473,672 | 10/1969 | Fincher | 211/51 |
| 3,870,150 | 3/1975 | Hummel | 206/438 |
| 4,034,853 | 7/1977 | Smith | 206/278 |
| 4,773,532 | 9/1988 | Stephenson | 206/278 |
| 4,844,293 | 7/1989 | McLaughlin | 211/34 |
| 4,993,589 | 2/1991 | McLaughlin | 221/33 |
| 5,025,503 | 6/1991 | O'Brien | 2/163 |
| 5,096,089 | 3/1992 | McLaughlin | 221/26 |
| 5,682,612 | 11/1997 | Schwarz | 2/161.6 |

FOREIGN PATENT DOCUMENTS 4126511  2/1992  Germany .................................. 221/33

*Primary Examiner*—William E. Terrell
*Assistant Examiner*—Gene O. Crawford
*Attorney, Agent, or Firm*—Jack C. Munro

[57] ABSTRACT

A dispenser for a stack of thin, disposable gloves wherein the gloves are placed within a box-like housing. Included within the housing is a biasing means which presses against the stack of gloves directly adjacent the access opening into the gloves. Each uppermost glove in the stack includes a spot of adhesive which is to connect with the directly underneath glove with this spot being located directly adjacent this access opening. Included within the box-like housing is a dispensing opening with the uppermost glove to partially protrude from this dispensing opening. The users hand is to be inserted into the glove with the glove then being extracted with the adhesive functioning to partially dispense the next glove in the stack of gloves and locate that in a position facilitating connection with a human hand.

19 Claims, 2 Drawing Sheets

DISPOSABLE GLOVE DISPENSER

BACKGROUND OF THE INVENTION

1) Field of the Invention

The field of this invention relates to disposable gloves and more particularly for a dispenser for such gloves.

2) Description of the Prior Art

Thin, gloves, generally constructed of plastic that are designed to be worn by humans, have been available commercially for several years. Such gloves are quite inexpensive and are intended to be used by any individual involved in a commercial endeavor where there is a possibility of transfer of disease or infection. For example, a common commercial endeavor would be in the food industry. Butchers, when cutting beef, are now required to wear disposable gloves, and if the butcher proceeds to then cut a chicken or turkey, the butcher is to discard the worn set of gloves and wear new gloves. The reason for this is to eliminate the possibility of the transfer of bacteria between the chicken, turkey and the beef. Also, in the fast food industry where individuals are preparing sandwiches and other foodstuffs, it is mandatory by government agencies that individuals involved in this business wear disposable, gloves. After each sandwich is prepared for a patron, the gloves are discarded and new gloves are then placed on the preparers hands.

Although the law requires that individuals wear gloves and frequently change these gloves when preparing of food, the non-wearing of such gloves is an exceedingly common occurrence. Although the food preparing establishment could be cited for breaking of the law, the law is not adhered to because the dispenser for the dispensing of such gloves does not make it convenient for the wearing of the gloves. The typical dispenser comprises placing of a folded quantity of the gloves in a box with there being an opening in the box through which a single glove is to be extracted. However, when an individual goes to extract a glove, it is quite common to extract several gloves at a time which commonly results in the unneeded gloves being discarded. Also, once a glove has been extracted, because the glove is constructed of such thin sheet material, it is difficult to open the glove and gain access into the interior of the glove in order to place one's hand within the glove. Therefore, it is a time consuming procedure to install a pair of gloves on one's hands. In certain industries, such as in fast food preparation, time is of the essence and the food preparers just do not have the time available to put gloves on multiple times each day.

SUMMARY OF THE INVENTION

There is a need to design a dispenser for disposable gloves where the dispenser facilitates the installation of the glove onto one's hand thereby making the installation of the glove convenient and, most importantly, quick.

Another objective of this invention is to construct a dispenser which can be manufactured inexpensively and therefore it does not significantly increase the cost of the thin, plastic gloves which would deter their widespread usage.

The dispenser of the present invention is constructed of a housing in a box-like configuration of a base and a top with the top interlocking with the base. Interiorly of the housing is an internal compartment within which is to be mounted a stack of thin, disposable gloves. Also, mounted within the internal compartment is a biasing device with a portion of the biasing device to rest on the stack of gloves with the resting point being directly adjacent the access opening into the gloves. Each of the gloves in the stack is to be adhesively secured to the adjacent glove in the stack with the adhesive not being permanent but permitting separation of the uppermost glove from the stack of gloves. The dispensing of the uppermost glove is to occur through a dispensing opening formed within the top of the housing. The access opening of the glove is to protrude and be exposed exteriorly of the dispensing opening and locate the uppermost glove in a position facilitating engagement with a user's hand. The top also is to include a pivotable, flap plate which is to function, when at-rest, to keep the gloves located in the stacked relationship, with this flap plate being pivotable to an out-of-the way position when dispensing of the uppermost glove from the stack of gloves. The top of the housing is to also include indicia in the form of a representation of a hand indicating to the user the position of entry of the hand in conjunction with the uppermost glove.

DETAILED DESCRIPTION OF THE PREFERRED EMBODIMENT

Figure 1:
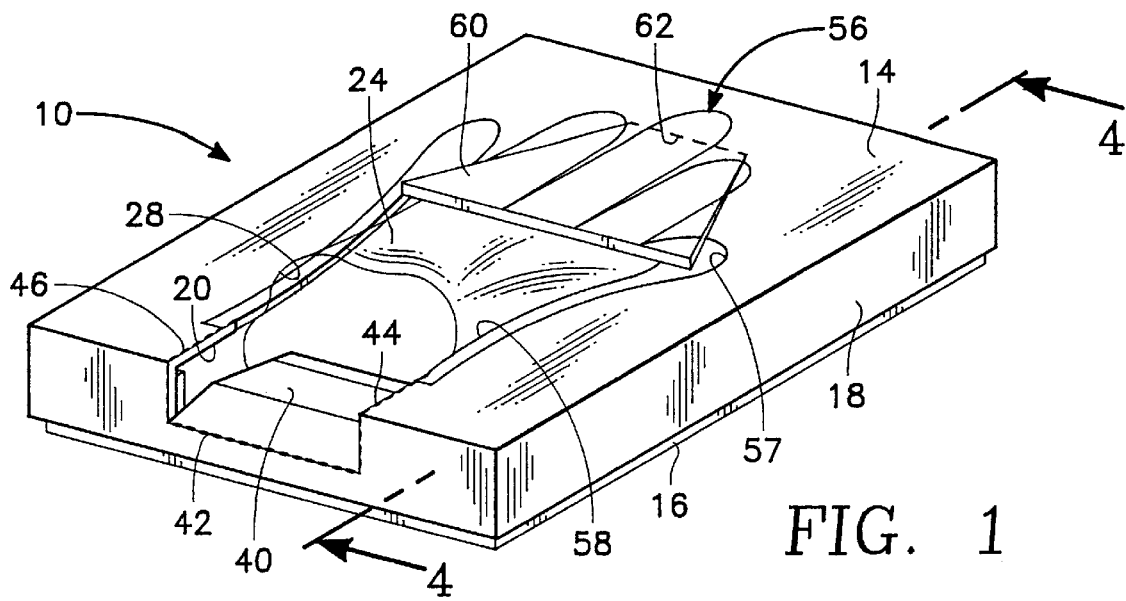
FIG. 1 is an isometric view of the dispenser of the present invention showing the uppermost glove of a stack of gloves in a position to be dispensed.

Referring particularly to the drawings, there is shown the dispenser 10 of this invention. The dispenser 10 is constructed to be in the form of a housing which is composed of a base 12 and a top 14. The housing is shown to be in a rectangular configuration. However, it is considered to be within the scope of this invention that other configurations other than rectangular could be used. The base 12 has an enclosing upstanding sidewall 16. The top 14 also has an enclosing downwardly extending sidewall 18. Sidewall 18 is to overlap sidewall 16 so as to interlockingly mount together the base 12 and the top 14 totally enclosing internal chamber 20. The housing could be constructed of a single walled box and not composed of the two separate sections of base 12 and top 14.

Located within the internal chamber 20, and placed against the base 12 is a stack 22 of thin, disposable gloves. The gloves 22 may be constructed of a polyethylene plastic and are so thin that they can be termed flimsy. Normally, in the stack 22, there will be initially placed a set quantity such as one hundred gloves. However, the initial number could be increased or decreased without departing from the scope of this invention. The gloves are of universal size and will fit everyone's hand with it to be understood that the glove is worn in a very loose fitting manner. The thickness of each of the gloves is just a few mils. The glove that is at the top of the stack 22 will be referred to as the uppermost glove 24. The glove that is directly underneath the uppermost glove 24 will be referred to as a further uppermost glove 26. The gloves in the stack 22 are arranged flat, and when observed from the top of the stack 22, resemble the shape of a hand.

At the rear edge of each of the gloves there is located an access opening 28 with only the access opening 28 being shown for the uppermost glove 24. The access opening for each of the gloves in the stack 22 are located in vertical alignment. Directly adjacent this vertical alignment of the access openings there is placed a roller 30 on the uppermost glove 24. The roller 30 generally will comprise no more than a two to three inch length of a hollow tube. Conducted through the hollow tube, which forms the roller 30, is an elastic member 32. The elastic member 32 is stretched somewhat taut with each end of the elastic member 32 being conducted through a hole 34 formed in the sidewall 16. It is to be understood that there are two in number of the holes 34 which are in transverse alignment with each other. The outer free end of each elastic member 32 is secured to a cap 36 with it being understood that there are two in number of the caps 36. A single cap 36 is located directly adjacent each hole 34. The caps 36 could be constructed of metal and physically deformed to press tightly against the elastic member 32 providing the securement between the elastic member 32 and each cap 36. The elastic member 32 is stretched somewhat taut between caps 36. The caps 36 rest against the exterior surface of the sidewall 16. Caps 36 are located directly adjacent the flat bottom base 12 so there is always a downwardly directed biasing force against the stack 22 even if there is only a single glove in the stack 22.

Figure 5:
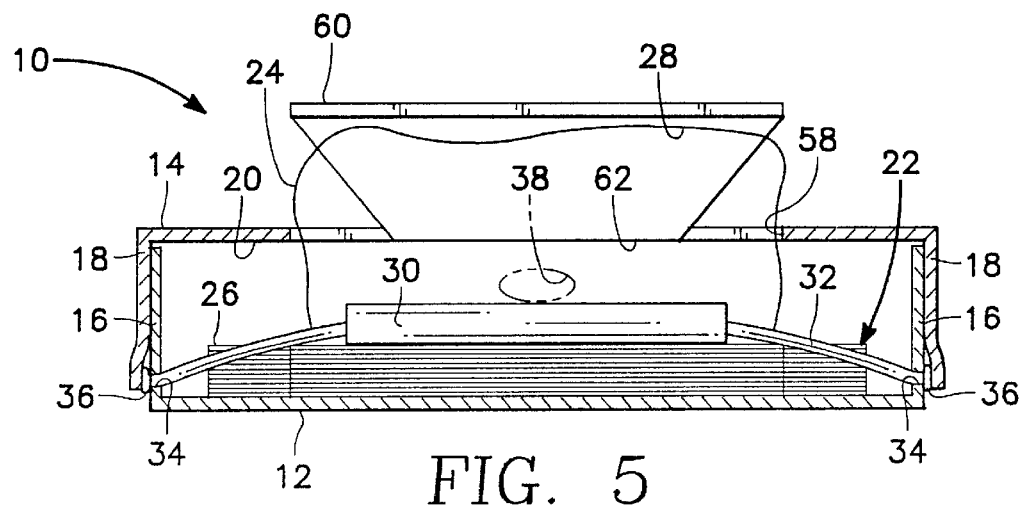
FIG. 5 is a transverse cross-sectional view taken along line 5—5 of FIG. 4.
Figure 6:
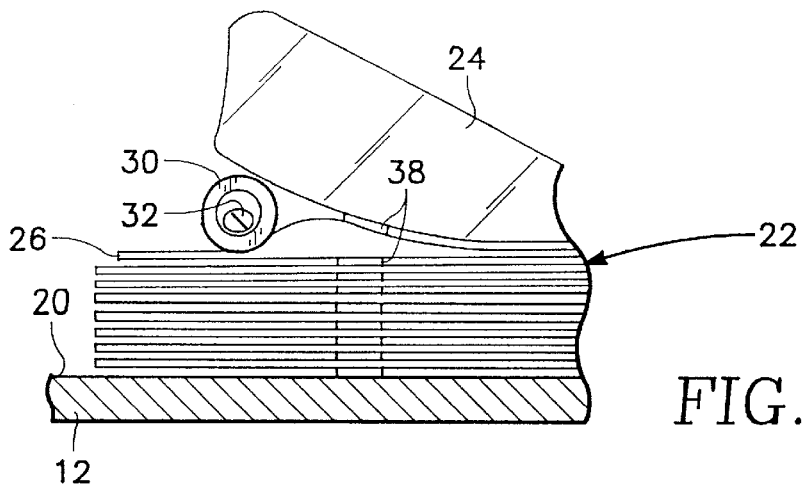
FIG. 6 is an enlarged cross-sectional view similar to the view of FIG. 4 showing in more detail the mounting arrangement of the stack of gloves in conjunction with a biasing device included within the dispenser with the biasing device being depicted in an unbiased state and the gloves in the stack of gloves being shown slightly separated strictly for the purpose of illustration.

The elastic member 32 functions to exert a biasing force causing the roller 30 to press down against the stack 22. It is the function of this biasing force to keep the stack 22 located in its exact position as shown in the drawings. Also, the biasing force produced against the roller 30 will allow the upper layer of the glove 24 to be moved upwardly to assume a spaced configuration from the lower layer of the uppermost glove 24 thereby opening of the access opening 28 is as clearly shown in FIGS. 1 and 5 of the drawings. During this extraction procedure of the upper layer, the roller 30 is rotated. Roller 30 permits unhindered extraction of the upper layer of the uppermost glove and also unhindered dispensing of the glove.

The lower layer of the uppermost glove 24 includes a spot of a tacky adhesive 38 with this tacky adhesive 38 to be in contact with the upper layer of the further uppermost glove 26. The reason for this adhesive 38 will be explained further on in the specification. It is to be understood that each glove that is located on top of another glove includes such a spot of adhesive 38. The adhesive 38 is not to be so strong as to be a permanent adhesion but merely a tacky adhesion. For the purpose of this invention, adhesive is meant to include a chemical composition, an ultrasonic weld, an adhesive tape or physical connection as by perforations.

Figures 2, 3:
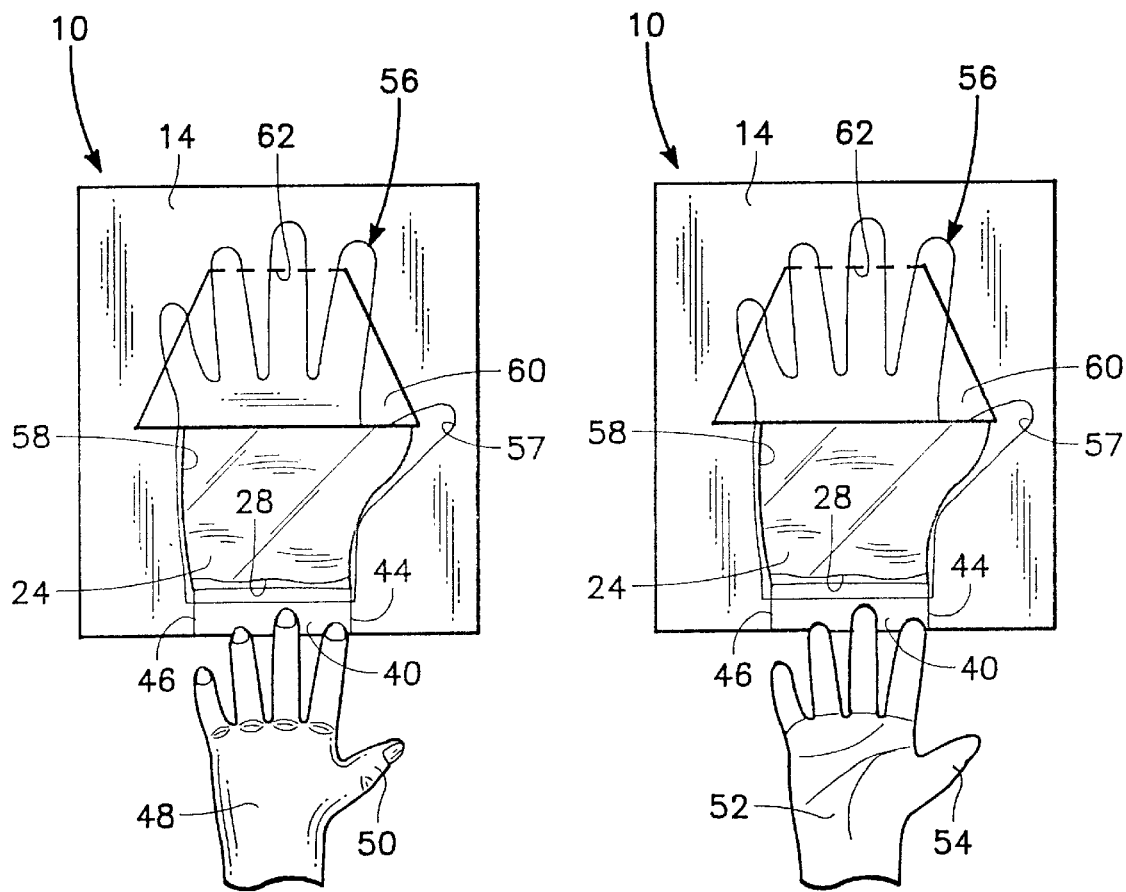
FIG. 2 is a top plan view depicting engagement of a left hand of a user in conjunction with the uppermost glove to be dispensed.
FIG. 3 is a top plan view depicting engagement of a right hand of a user in conjunction with the uppermost glove to be dispensed.

The front section of the sidewall 18 includes a fold-down flap 40. The fold-down flap 40 is produced by a score line 42 and perforated side lines 44 and 46. A similar fold-down flap (not shown) is formed within the sidewall 16 with the fold-down flap in sidewall 18 being in alignment with the fold-down flap 40. It is intended for the user when placing of the dispenser 10 in usage, to deflect the fold-down flap 40 and the same flap on sidewall 16 as by breaking perforated lines 44 and 46. The purpose of deflecting of the fold-down flap 40 and flap on sidewall 16 is to position lower the wall area directly adjacent the access opening 28 in order to make it easier for the individual 40 slide his or her hand, such as left hand 48 into the access opening 28, as shown in FIG. 2 of the drawings. The hand 48 is to be slipped into the access opening 28 so that the thumb 50 of the left hand 48 will align with the thumb area of the uppermost glove 24. When it is desired to place the uppermost glove on the right hand 52, the right hand 52 is turned upside down as opposed to the left hand 48 so that the thumb 54 of the right hand 52 will again align with the thumb area of the uppermost glove 24.

Figure 4:
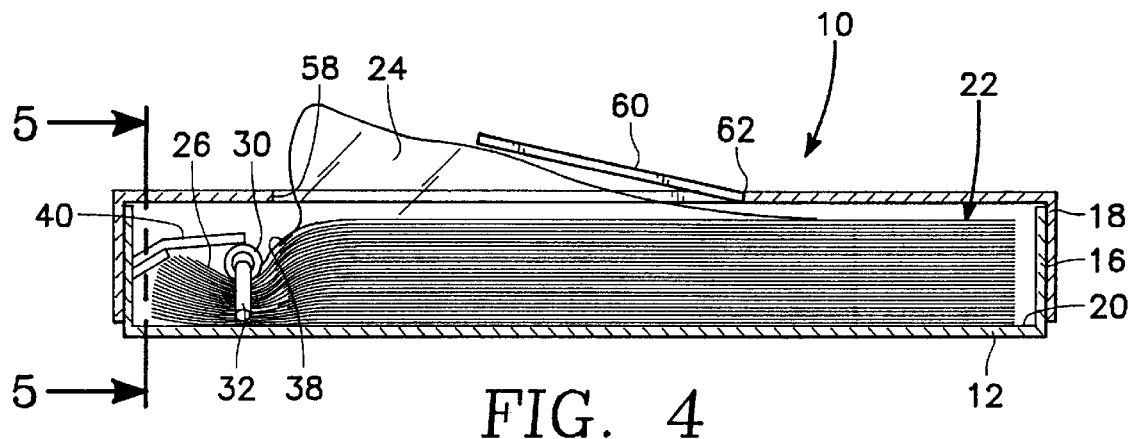
FIG. 4 is a longitudinal cross-sectional view taken along line 4—4 of FIG. 1.

In order to give an indication to the user as to what direction the hand is to be inserted within the access opening 28, there is an inscribed indicia 56 in the form of a representation of a hand on the top 14. All the user needs to do is align his or her thumb so that it enters the access opening 28 so the thumb will align with the thumb portion 57 of the indicia 56. In order to insure that the uppermost glove 24 does not become accidentally dislodged from the dispensing opening 58 formed within the top 14, there is mounted on the top 14 a flap plate 60. The flap plate 60 is attached to the top 14 at a score line 62 which function as a hinge axis. A natural tendency will be for the flap plate 60 to rest against the uppermost glove 24 tending to keep the gloves in the stack 22. However, once the individuals hand has been placed within the access opening 28 and totally inserted within the uppermost glove 24, the flap plate 60 will hingedly move in a clockwise direction as shown in FIG. 4 of the drawings. Then when the uppermost glove 24 is dispensed through the dispensing opening 58 by being extracted from the stack 22, the flap plate 60 will pivot further in a clockwise direction so as to provide the necessary clearance for the extraction of the uppermost glove 24. During the extraction procedure of the uppermost glove 24, the spot of adhesive 38 that is on the upper layer of the further uppermost glove 26 will pull this layer to an extracted position and be caused to protrude through the dispensing opening 58. This will locate the now further uppermost glove in a position that facilitates insertion of the users hand therein not requiring the user to physically separate the layers of the glove in order to insert ones hand. Further outward dispensing movement of the uppermost glove 24 will cause the uppermost glove 24 to separate from the further uppermost glove by release of adhesive 38.

It can thus be seen that the primary advantage to the dispenser 10 of this invention is that the uppermost glove 24 is always located in a position that permits direct insertion of ones hand into the glove and then extraction of the glove that is now located on the hand from the dispenser 10. The only movements in order to place a glove on the hand is to the inserting of ones hand within the glove and then extracting the glove. The result is that it is a most quick procedure to install a glove on ones hand, and actually an individual can place a glove on each hand within a matter of a couple of seconds. This type of quick installation procedure is almost imperative in order for the thin, disposable gloves to be used where required by law on a widespread basis.

It is considered to be within the scope of this invention that the cap 36 could be eliminated, and the elastic member 32 could be a continuous elastic member that extends across the base 12. It is to be understood that the hand indicia 56 in part is inscribed on the flap plate 60.

When the dispenser 10 of this invention is initially supplied to the user, the dispensing opening 58 is covered by a cover (not shown). The cover is to be removed and discarded. Pressure is then applied to fold-down flap 40 breaking perforated lines 44 and 46 with fold-down flaps 40 and similar flap on sidewall 16 being moved down and against the stack 22. The uppermost glove 24 is then caused to protrude from opening 58 placing access opening in the open position. The dispenser 10 is now ready for use.

What is claimed is:

1. A dispenser for disposable gloves comprising:

a housing having an internal chamber;

a stack of a plurality of said disposable gloves being located within said internal chamber, said stack having an uppermost glove;

biasing means mounted on said housing applying pressure against said stack, said biasing means being in contact with said uppermost glove; and said housing being capable of totally enclosing said stack, said housing having an openable dispensing opening through which protrudes an upper layer of said uppermost glove, said upper layer to be disengaged from said biasing means when said uppermost glove is in a to-be-dispensed position, whereby a persons hand is to be inserted into said uppermost glove when in said to-be-dispensed position and then said most uppermost glove is to be removed from said stack exposing a further uppermost glove.

2. The dispenser as defined in claim 1 wherein:

said housing being formed of a base and a top with said base and said top interlocking together to form an enclosed container.

3. The dispenser as defined in claim 1 wherein:

each of said gloves having an access opening permitting entry of a persons hand, said biasing means being mounted on said uppermost glove directly adjacent said access opening.

4. The dispenser as defined in claim 1 wherein:

said housing including indicia in the form of a representation of a human hand, said indicia connecting with said dispensing opening, said indicia including a thumb portion, whereby when a user inserts a hand into said uppermost glove the user's thumb is to be aligned with said thumb position.

5. The dispenser as defined in claim 1 wherein:

said biasing means including a roller, said roller being low frictionally rotatable on said biasing means, said roller to be in direct contact with said uppermost glove, said roller rotating on said biasing means when said uppermost glove is extracted from said stack.

6. The dispenser as defined in claim 5 wherein:

said biasing means includes an elastic member, said roller being mounted on said elastic member, said elastic member to apply a force against said roller maintaining said roller in contact with said stack.

7. The dispenser as defined in claim 1 wherein:

said uppermost glove including an adhesive, said uppermost glove having an access opening to permit entry of a persons hand, said adhesive located directly adjacent said access opening, said adhesive functioning to temporarily secure said uppermost glove to said further uppermost glove, whereby when said uppermost glove is removed from said stack said adhesive functions to dislodge an upper layer of said further uppermost glove from said biasing means and locate said access opening of said further uppermost glove in an open position to facilitate connection with a persons hand.

8. The dispenser as defined in claim 7 wherein:

said biasing means including a roller, said roller being low frictionally rotatable on said biasing means, said roller to be in direct contact with said uppermost glove, said roller rotating on said biasing means when said uppermost glove is extracted from said stack.

9. The dispenser as defined in claim 8 wherein:

said biasing means includes an elastic member, said roller being mounted on said elastic member, said elastic member to apply a force against said roller maintaining said roller in contact with said stack.

10. The dispenser as defined in claim 9 wherein:

each of said gloves having an access opening permitting entry of a persons hand, said biasing means being mounted on said uppermost glove directly adjacent said access opening.

11. The dispenser as defined in claim 10 wherein:

said housing including indicia in the form of a representation of a human hand, said indicia connecting with said dispensing opening, said indicia including a thumb portion, whereby when a user inserts a hand into said uppermost glove the user's thumb is to be aligned with said thumb position.

12. A dispenser for thin, disposable gloves comprising:

a housing having an internal chamber;

a stack of a plurality of said disposable gloves being located within said internal chamber, said stack having an uppermost glove;

biasing means applying pressure against said stack, said biasing means being in contact with said uppermost glove;

said housing having a dispensing opening through which protrudes an upper layer of said uppermost glove, said upper layer to be disengaged from said biasing means, whereby a persons hand is to be inserted into said uppermost glove while in connection with said stack and then said most uppermost glove is to be removed from said stack exposing a further uppermost glove; and a flap plate mounted on said housing, said flap plate being capable of limited pivoting movement relative to said housing, said flap plate being mounted in conjunction with said dispensing opening and functioning to cover a portion of said dispensing opening and also a portion of said uppermost glove, said flap plate having a normal at-rest position tending to maintain said uppermost glove in contact with said stack, during disengagement of said uppermost glove from said stack said flap plate pivoting in a direction away from said housing to permit free disengagement of said uppermost glove from said stack.

13. A dispenser for thin, disposable gloves comprising:

a housing having an internal chamber;

a stack of a plurality of said disposable gloves being located within said internal chamber, said stack having an uppermost glove;

biasing means applying pressure against said stack, said biasing means being in contact with said uppermost glove;

said housing having a dispensing opening through which protrudes an upper layer of said uppermost glove, said upper layer to be disengaged from said biasing means, whereby a persons hand is to be inserted into said uppermost glove while in connection with said stack and then said most uppermost glove is to be removed from said stack exposing a further uppermost glove;

said uppermost glove including an adhesive, said uppermost glove having an access opening to permit entry of a persons hand, said adhesive located directly adjacent said access opening, said adhesive functioning to temporarily secure said uppermost glove to said further uppermost glove, whereby when said uppermost glove is removed from said stack said adhesive functions to dislodge an upper layer of said further uppermost glove from said biasing means and locate said access opening of said further uppermost glove in an open position to facilitate connection with a persons hand;

said biasing means including a roller, said roller being low frictionally rotatable on said biasing means, said roller to be in direct contact with said uppermost glove, said roller rotating on said biasing means when said uppermost glove is extracted from said stack;

said biasing means includes an elastic member, said roller being mounted on said elastic member;

each of said gloves having an access opening permitting entry of a persons hand, said biasing means being mounted on said uppermost glove directly adjacent said access opening;

said housing including indicia in the form of a representation of a human hand, said indicia connecting with said dispensing opening; and a flap plate mounted on said housing, said flap plate being capable of limited pivoting movement relative to said housing, said flap plate being mounted in conjunction with said dispensing opening and functioning to cover a portion of said opening and also a portion of said uppermost glove, said flat plate having a normal at-rest position tending to maintain said uppermost glove in contact with said stack, during disengagement of said uppermost glove from said stack said flap plate pivoting in a direction away from said housing to permit free disengagement of said uppermost glove from said stack.

14. The dispenser as defined in claim 13 wherein:

said housing being formed of a base and a top with said base and said interlocking together to form an enclosed container.

15. A dispenser for disposable gloves comprising:

a housing having an internal chamber;

a stack of a plurality of said disposable gloves being located within said internal chamber, said stack having an uppermost glove;

means for holding said stack in its stacked position said means being mounted on said housing;

said housing being capable of totally enclosing said stack, said housing having an openable dispensing opening through which protrudes an upper layer of said uppermost glove, said upper layer to be disengaged from said means when said uppermost glove is in a to-be-dispensed position, whereby a persons hand is to be inserted into said uppermost glove when in said to-be-dispensed position and then said uppermost glove is to be removed from said stack exposing a further uppermost glove; and said housing including indicia in the form of a representation of a human hand, said indicia connecting with said dispensing opening, said indicia including a thumb portion, whereby when a user inserts a hand into said uppermost glove the user's thumb is to be aligned with said thumb portion.

16. The dispenser as defined in claim 15 wherein:

a fold-down flap formed within said housing, said fold-down flap to be deflected to a lower position when placing said dispenser in usage.

17. The dispenser as defined in claim 15 wherein:

said uppermost glove including an adhesive, said uppermost glove having an access opening to permit entry of a persons hand, said adhesive located directly adjacent said access opening, said adhesive functioning to temporarily secure said uppermost glove to said further uppermost glove, whereby when said uppermost glove is removed from said stack said adhesive functions to dislodge an upper layer of said further uppermost glove from said means and locate said access opening of said further uppermost glove in an open position to facilitate connection with a persons hand.

18. A dispenser for thin, disposable gloves comprising:

a housing having an internal chamber;

a stack of a plurality of said disposable gloves being located within said internal chamber, said stack having an uppermost glove;

means for holding said stack in its stacked position;

said housing having a dispensing opening through which protrudes an upper layer of said uppermost glove, said upper layer to be disengaged from said means, whereby a persons hand is to be inserted into said uppermost glove while in connection with said stack and then said most uppermost glove is to be removed from said stack exposing a further up permost glove; and a flap plate mounted on said housing, said flap plate being capable of limited pivoting movement relative to said housing, said flap plate being mounted in conjunction with said dispensing opening and functioning to cover a portion of said dispensing opening and also a portion of said uppermost glove, said flap plate having a normal at-rest position tending to maintain said uppermost glove in contact with said stack, during disengagement of said uppermost glove from said stack said flap plate pivoting in a direction away from said housing to permit free disengagement of said uppermost glove from said stack.

19. The dispenser as defined in claim 18 wherein:

a fold-down flap formed within said housing, said fold-down flap to be deflected to a lower position when placing said dispenser in usage, said fold-down flap being connected to said flap plate prior to said fold-down flap being deflected and when said flap plate is in said at-rest position.

\* \* \* \* \*